United States Patent
Zemlin

(10) Patent No.: US 12,295,652 B2
(45) Date of Patent: *May 13, 2025

(54) ABLATION OF MYOCARDIAL TISSUES WITH NANOSECOND PULSED ELECTRIC FIELDS

(71) Applicant: Old Dominion University Research Foundation, Norfolk, VA (US)

(72) Inventor: Christian W. Zemlin, Norfolk, VA (US)

(73) Assignee: OLD DOMINION UNIVERSITY RESEARCH FOUNDATION, Norfolk, VA (US)

(*) Notice: Subject to any disclaimer, the term of this patent is extended or adjusted under 35 U.S.C. 154(b) by 49 days.

This patent is subject to a terminal disclaimer.

(21) Appl. No.: 18/307,051

(22) Filed: Apr. 26, 2023

(65) Prior Publication Data
US 2023/0277241 A1 Sep. 7, 2023

Related U.S. Application Data

(63) Continuation of application No. 17/006,406, filed on Aug. 28, 2020, now Pat. No. 11,672,594, which is a
(Continued)

(51) Int. Cl.
*A61B 18/14* (2006.01)
*A61B 18/00* (2006.01)

(52) U.S. Cl.
CPC .............. *A61B 18/1492* (2013.01); *A61B 2018/00357* (2013.01); *A61B 2018/00363* (2013.01);
(Continued)

(58) Field of Classification Search
CPC ............ A61B 18/1477; A61B 18/1492; A61B 2018/00357; A61B 2018/00363; A61B 2018/00577; A61B 2018/00613

See application file for complete search history.

(56) References Cited

U.S. PATENT DOCUMENTS

| 6,514,250 B1 | 2/2003 | Jahns et al. |
| 6,652,518 B2 | 11/2003 | Wellman et al. |

(Continued)

FOREIGN PATENT DOCUMENTS

WO 2013/019385 2/2013

OTHER PUBLICATIONS

Latchamsetty et al., Ablation of Atrial Fibrillation Using an Irrigated-Tip Catheter: Open or Closed?, PACE, vol. 35, 2012, pp. 503-505.
(Continued)

*Primary Examiner* — Michael F Peffley
(74) *Attorney, Agent, or Firm* — MH2 Technology Law Group, LLP

(57) ABSTRACT

An apparatus and methods for performing ablation of myocardial tissues are disclosed. The apparatus includes a plurality of ablation electrode configurations to which nanosecond pulsed electric fields are applied. The methods relate to therapies to treat cardiac arrhythmias, such as, atrial fibrillation and scar-related ventricular tachycardia, amongst others. The affected myocardial tissues are ablated creating a plurality of lesions enabled by the nanosecond pulsed electric fields applied to either penetrating electrodes, endo-endo electrodes, or endo-epi electrodes. Different electrophysiological tests are performed to assess the application of nanosecond pulsed electric field ablation to specific desired tissue location within the heart. Test results show the potential to overcome limitations of current ablation therapies, thereby providing patients and doctors a superior treatment for cardiac arrhythmias.

25 Claims, 13 Drawing Sheets

Related U.S. Application Data continuation of application No. 15/885,930, filed on Feb. 1, 2018, now Pat. No. 10,786,303, which is a continuation of application No. 14/604,400, filed on Jan. 23, 2015, now Pat. No. 9,918,790.

(60) Provisional application No. 61/930,766, filed on Jan. 23, 2014.

(52) U.S. Cl.
CPC ............. *A61B 2018/00577* (2013.01); *A61B 2018/00613* (2013.01); *A61B 18/1477* (2013.01)

(56) References Cited

U.S. PATENT DOCUMENTS

| | | | |
|---|---|---|---|
| 6,795,728 B2* | 9/2004 | Chornenky | A61N 1/328 607/2 |
| 6,827,714 B2 | 12/2004 | Swanson | |
| 7,435,247 B2 | 10/2008 | Woloszko et al. | |
| 7,892,230 B2 | 2/2011 | Woloszko | |
| 8,100,899 B2* | 1/2012 | Doty | A61B 18/1442 606/49 |
| 2004/0162551 A1 | 8/2004 | Brown et al. | |
| 2005/0261672 A1* | 11/2005 | Deem | A61B 18/1492 606/41 |
| 2009/0062788 A1* | 3/2009 | Long | A61B 18/14 606/41 |
| 2010/0023004 A1 | 1/2010 | Francischelli | |
| 2012/0059255 A1 | 3/2012 | Paul et al. | |
| 2013/0030430 A1 | 1/2013 | Stewart | |
| 2013/0172864 A1* | 7/2013 | Ibrahim | A61B 18/1492 606/1 |
| 2016/0184003 A1 | 6/2016 | Srimathveeravalli et al. | |

OTHER PUBLICATIONS

Roger et al., Heart Disease and Stroke Statistics—2011 Update: A Report From the American Heart Association, Circulation. 2011;123:e18-e209, https://doi.org/10.1161/CIR.0b013e3182009701, pp. 1-284.
Marini et al., Contribution of Atrial Fibrillation to Incidence and Outcome of Ischemic Stroke Results From a Population-Based Study, Stroke 2005, DOI: 10.1161/01.STR.0000166053.83476.4a, pp. 1115-1119.
Go et al., Prevalance of Diagnosed Atrial Fibrillation in Adults National Implications for Rythm Management and Stroke Prevention: the AnTicoagulation and Risk Factors in Atrial Fibrillation (ATRIA) Study, JAMA, May 9, 2001, vol. 285, No. 18 (Reprinted), pp. 2370-2375.
Thrall et al., Quality of Life in Patients with Atrial Fibrillation: A Systematic Review, The American Journal of Medicine (2006) 119, pp. 448.e1-448.e19.
Deneke et al., Intra-operative cooled-tip radiofrequency linear atrial ablation to treat permanent atrial fibrillation, European Heart Journal (2007) 28, doi:10.1093/eurheartj/ehm397, pp. 2909-2914.
Ng et al., Catheter Ablation of Atrial Fibrillation, Clin. Cardiol. 25, 2002, pp. 384-394.
Blaufox et al., Catheter Ablation of Tachyarrhthmias in Small Children, Indian Pacing and Electrophysiology Journal (ISSN 0972-6292), 2005, 5(1), pp. 51-62.
Hugh Calkins, Catheter Ablation to Maintain Sinus Rhythm, Circulation, 125, 2012, https://doi.org/10.1161/ CIRCULATIONAHA.111.019943, pp. 1439-1445.
Hornero et al., Intraoperative Cryoablation of Atrial Fibrillation With the Old-Fashioned Cryode Tips: A Simple, Effective, and Inexpensive Method, Ann Thorac Surg , 84, 2007, pp. 1408-1411.
Erez et al., Controlled Destruction and Temperature Distributions in Biological Tissues Subjected to Monoactive Electrocoagulation, J Biomech Eng, vol. 102, 1980, pp. 42-49.
Naccarelli et al., Increasing Prevalence of Atrial Fibrillation and Flutter in the United States, Am J Cardiol 104, 2009, pp. 1534-1539.
Vest et al., Clinical Use of Cooled Radiofrequency Ablation, Journal of Cardiovascular Electrophysiology vol. 19, No. 7, Jul. 2008, pp. 769-773.
Deodhar, Ajita et al., Irreversible Electroporation Near the Heart: Ventricular Arrhythmias Can Be Prevented With ECG Synchronization, American J. of Roentgenology, 196.3 (2011, W330-W335.
Lavee, Jacob et al., A Novel Nonthermal Energy Source for Surgical Epicardial Atrial Ablation: Irreversible Electroporation, The Heart Surgery Forum, 2007, vol. 10, No. 2, pp. 96-101.
Maor, Elad et al., Non Thermal Irreversible Electroporation: Novel Technology for Vascular Smooth Muscle Cells Ablation, PLoS One, Mar. 2009, vol. 4, Issue 3, e4757, pp. 1-9.

* cited by examiner

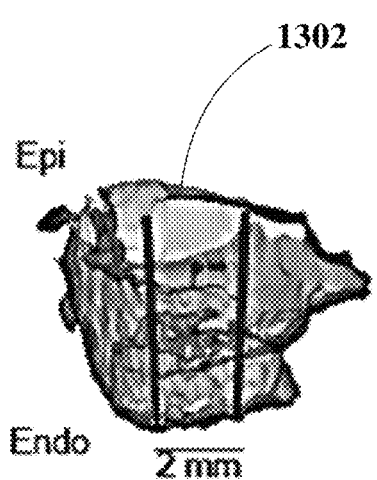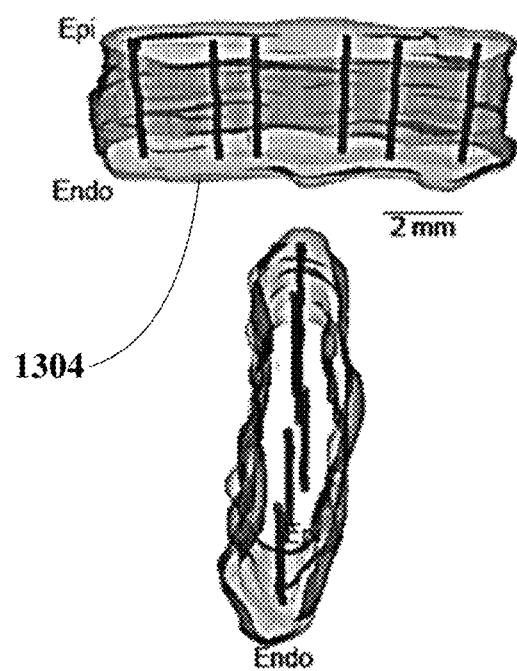
FIG. 13A
FIG. 13B
FIG. 13

ABLATION OF MYOCARDIAL TISSUES WITH NANOSECOND PULSED ELECTRIC FIELDS

CROSS-REFERENCE TO RELATED APPLICATIONS

This application is a continuation of co-pending U.S. application Ser. No. 17/006,406, filed Aug. 28, 2020 and entitled "Ablation of Myocardial Tissues with Nanosecond Pulsed Electric Fields" and now issued as U.S. Pat. No. 11,672,594, which is a continuation of U.S. application Ser. No. 15/885,930, filed Feb. 1, 2018 and now issued as U.S. Pat. No. 10,786,303 entitled "Ablation of Myocardial Tissues with Nanosecond Pulsed Electric Fields", which is a continuation of U.S. application Ser. No. 14/604,400, filed Jan. 23, 2015 and now issued as U.S. Pat. No. 9,918,790 entitled "Ablation of Myocardial Tissues with Nanosecond Pulsed Electric Fields", which claims the benefit of U.S. Provisional Application No. 61/930,766 filed Jan. 23, 2014 and entitled "Nanosecond Pulsed Electric Fields Ablation", the entire contents of all of which are incorporated herein by reference.

BACKGROUND

Field of the Disclosure

The present disclosure relates generally to ablation, and more specifically, to systems and methods for biological tissue ablation using nanosecond pulsed electric fields.

Background Information

Four major types of radio frequency (RF) catheter ablation systems are currently used for treatment of myocardial tissues. These types of ablation systems are identified according to the type of catheters employed by each system. For example: (1) Standard 4-mm-tip catheters; (2) large 8-10-mm-tip catheters; (3) open-loop irrigated-tip catheters; and (4) closed-loop irrigated-tip catheters [1].

Ablation of myocardial tissue is especially important for the treatment of atrial fibrillation (AF), which is one of the most common cardiac arrhythmias. In the United States, more than 3 million patients are affected by AF [2]. Most of these patients have seen their quality of life significantly reduced. For example, patients experiencing AF experience a fivefold increase in the risk of stroke with approximately 15% of all strokes nationwide being caused by AF [3-6].

Upon a diagnosis of AF, typically the first therapy prescribed for AF patients is pharmacological. Unfortunately, pharmacological therapy only yields satisfactory results in about half of the patients so prescribed [5]. For the remaining half of patients, the most common therapy is radiofrequency (RF) ablation. RF ablation is a procedure in which conduction-blocking lesions of destroyed (or ablated) tissue are created in the atria in order to stop AF [7]. RF ablation is performed by applying heat via an intra-atrial catheter to the endocardium until the tissue around the catheter is destroyed, thereby creating an ablated patch of tissue. The catheter is then repositioned and the procedure repeated. If the series of ablated patches of tissue is spaced tightly enough, a non-conducting lesion is created. Typically, lesions are created around the pulmonary veins in the left atria where AF most frequently originates and several more linear lesions are created to prevent AF from reoccurring [8]. Approximately 100,000 patients in the United States receive RF ablation therapy every year [9].

In addition to AF, scar-related ventricular tachycardia (VT) is another disease associated with a high mortality rate. VT ablation is a procedure in which conduction-blocking lesions of destroyed (or ablated) tissue are created in the ventricle in order to stop VT. For VT, ventricular ablation using RF is an important therapy [10].

Even though therapy by RF ablation is state of the art technology, it exhibits a number of well-known drawbacks discussed below:

1) Recurrence

Recurrence is considered the greatest challenge for RF ablation as many patients whose AF has been removed with RF ablation develop it again within months or a few years' time. Approximately 20% to 50% of treated patients eventually suffer from recurrence [11]. The underlying reason for recurrent AF is because the lesions created during the RF ablation procedure become conductive again due to the limited control over the geometry of the ablated volume (e.g., created lesions do not exhibit a consistent width) during the RF ablation procedure.

2) Thermal Side Effects

In RF ablation, overheating is the means by which tissue is rendered inactive or destroyed. The minimum temperature range necessary for ablation is approximately 45° C. to 50° C. for several seconds duration [12]. During RF ablation, at least part of the tissue is heated to 70° C. or more. Thermal side effects include the formation of blood clots (e.g., thrombus formation), charring, steam pops, and thermal damage to adjacent tissues, such as the esophagus.

To allow the application of higher power without endocardial overheating, different active cooling strategies have been developed. These strategies include circulating cooling liquid inside the tip of the catheter (closed irrigation), or expelling the cooling liquid through small holes at the tip of the catheter (open irrigation), such as saline solution. While irrigated catheters maintain the catheter tip temperature and the tissue surface temperature at substantially lower temperatures, thermal side effects remain a major concern.

Recently, cryoablation has evolved as an alternative to RF ablation. Cryoablation reduces the thermal side effects of RF ablation. Cryoablation exhibits drawbacks including phrenic nerve palsy, longer ablation times, and lower control of the ablated volume than RF ablation. Additionally, another limitation of using cryoablation is that the endocardial freezing process needs a bloodless field and the lesion created is not a complete transmural lesion as is created during RF ablation [13].

3) Long Duration of Procedure

RF lesions are created point by point, and a single application can yield an ablated volume measuring approximately 5 mm to 10 mm in diameter. A full ablation procedure can require well over 100 applications. Additionally, the heating time in a single application is generally from 15 seconds to 60 seconds. Therefore, a single RF ablation procedure for AF can take from 2.5 hours to 3.0 hours.

In view of the above identified limitations associated with current ablation systems in treating myocardial tissue, there is a need for new systems and methods with enhanced efficacy that enable therapies reducing risk to patients.

SUMMARY

The embodiments of the present disclosure describe systems and methods for performing ablation of cardiac tissues using nanosecond pulsed electric fields (nsPEFs). According to some embodiments, the system includes a plurality of electrode configurations and a pulser circuit configured to generate and deliver voltage pulses to the electrode configurations so that the resulting electric field between the electrodes is a nanosecond pulsed electric field of the desired amplitude and frequency.

In the present disclosure, the ablation of cardiac tissue is performed by the application of intense nsPEFs for very short durations. Ablation with nsPEFs addresses the majority, if not all, of the limitations encountered using RF ablation as well as cryoablation. Ablation with nsPEFs provides treatments and therapies for a plurality of arrhythmia conditions, such as, for example atrial fibrillation, ventricular tachycardia, and other arrhythmias.

In some embodiments, using nsPEF ablation results in more precise control of the ablation volume as compared to the use of RF ablation. In these embodiments, improved control of the ablation volume is achieved because the electrical fields generated during nsPEF ablation drop off much more sharply at the boundaries of the ablation volume when using the disclosed electrode configurations as compared to RF ablation where temperature routinely causes tissue damage beyond the intended ablation volume because heat is diffusing from the site of the RF ablation catheter. Further to these embodiments, the increased control aspects of nsPEF ablation reduce the high recurrence rate experienced when utilizing RF ablation. Additionally, ablation of cardiac tissue using nsPEF ablation can ensure a more uniform lesion thickness thereby reducing the likelihood of the recurrence of Atrial Fibrillation (AF).

In some embodiments, the interaction of nsPEFs with untreated tissue to produce ablated tissue is by means of electroporating the outer cell membranes of the untreated tissue. In other embodiments, the interaction of nsPEFs with untreated tissue to produce ablated tissue is by means of electroporating membranes inside the cells. In an exemplary embodiment, the pulser circuit of the system generates voltage pulses with a pulse duration from about 1 ns to about 1000 ns. Further to this exemplary embodiment, the pulser circuit generates the voltage pulses with a pulse amplitude from about 1 kV to about 100 kV. Further to these embodiments, the resultant nsPEF energy deposited within the cardiac tissue does not result in thermal side effects as occurs when using RF ablation. This is because the increase in temperature resulting from a small number of pulses (typically 5 pulses) of the given specifications is typically less than 1° C., even in the immediate vicinity of the electrodes.

In some embodiments, nsPEF ablation is performed at specific tissue location sites for a duration from about 1 second to about 2 seconds per site treated. This compares to RF ablation techniques that generally require durations from about 15 seconds to about 60 seconds. nsPEF ablation significantly reduces treatment time and is a major improvement for both the individual patient and the ablation treatment centers where increased capacity will lead to rapidly satisfying the demand for ablation procedures.

In an embodiment, a penetrating configuration of electrodes and a method for ablating myocardial tissue using nsPEFs are described. In this embodiment, the penetrating configuration of electrodes includes two thin substantially parallel electrodes that are inserted into the endocardium portion of the tissue, proximate to one another, all the way through the tissue wall.

In another embodiment, an endo-endo configuration of electrodes and a method for ablating myocardial tissue using nsPEF are described. In this embodiment, the endo-endo configuration of electrodes includes a first electrode located at a first surface location of an endocardium and a second electrode located at a second surface location of the endocardium proximate to the first surface location. In other embodiments, the first electrode and the second electrode are placed so as to be in substantially parallel orientation.

In a further embodiment, an endo-epi configuration of electrodes and a method for ablating myocardial tissue using nsPEF are described. In this embodiment, the endo-epi configuration of electrodes includes a first electrode located on the surface of an endocardium and a second electrode located on the surface of the epicardium substantially opposite to the location of the first electrode located on the surface of the epicardium. In other words, the first electrode and the second electrode are placed so that they extend substantially collinearly.

In some embodiments, a general advantage of the electrode configurations is the improved control and uniformity of the volume and boundary of ablated tissue.

In some embodiments, multiple designs of electrode configurations for nsPEF ablation of myocardial tissues are disclosed and particular electrode configurations are recommended for use in producing specific types of lesions. Further to these embodiments, a plurality of lesions is described that includes methods for creating the specific lesions by employing the different electrode configurations as well as different procedures (e.g., side-by-side, interwoven, sideways, and the like) in conjunction with nsPEF ablation for treatment of myocardial tissues.

According to embodiments in the present disclosure, a series of tests can be performed to assess the results obtained from nsPEF ablation of myocardial tissues. In these embodiments, the tests include optical mapping of the heart, which involves illuminating the heart with laser light and recording the fluorescence of voltage-sensitive dyes, electrophysiological analysis of lesions, and propidium iodide fluorescence for the tridimensional reconstruction of lesion geometry, amongst others. Further to these embodiments, the tests assess the results of the formation of lesions in the cardiac tissue from nsPEF ablation.

The present disclosure leads to enhanced treatments of a plurality of cardiac arrhythmias, especially atrial fibrillation (AF). The significant results from various tests confirm that nsPEF ablation of myocardial tissues is a treatment that addresses all of the drawbacks in current art. In an aspect of the present disclosure, the risk to patients from using nsPEF ablation methods is reduced since many risks depend directly on the length and cost of the procedure.

BRIEF DESCRIPTION OF THE DRAWINGS

FIG. 7 is a graphical representation illustrating methods of combining single ablations to yield at least one lesion within the myocardial tissue using either the penetrating electrode configuration or the endo-endo electrode configuration and incorporating nsPEFs, according to some embodiments.

FIG. 8A is a photographic representation depicting a pulse application using a penetrating electrode configuration implemented with tungsten wires to create lesions within heart ventricle tissue and incorporating nsPEFs, according to an embodiment.

FIG. 8B is a photographic representation depicting a heart after nsPEF application with nsPEF according to an embodiment; the electrode positions are marked with surgical ink.

FIG. 13 includes graphical representations illustrating 3D reconstructions of lesions created using a single pulse application and multiple pulse applications that are implemented using a penetrating electrode configuration that incorporates nsPEFs, according to various embodiments.

FIG. 13A is a graphical representation depicting a 3D reconstruction of a lesion created using a single pulse application implementing a penetrating electrode configuration and incorporating nsPEFs, according to an embodiment.

FIG. 13B is a graphical representation depicting a 3D reconstruction of lesions created using multiple pulse applications implementing a penetrating electrode configuration and incorporating nsPEFs, according to an embodiment.

DETAILED DESCRIPTION

Figure 1:
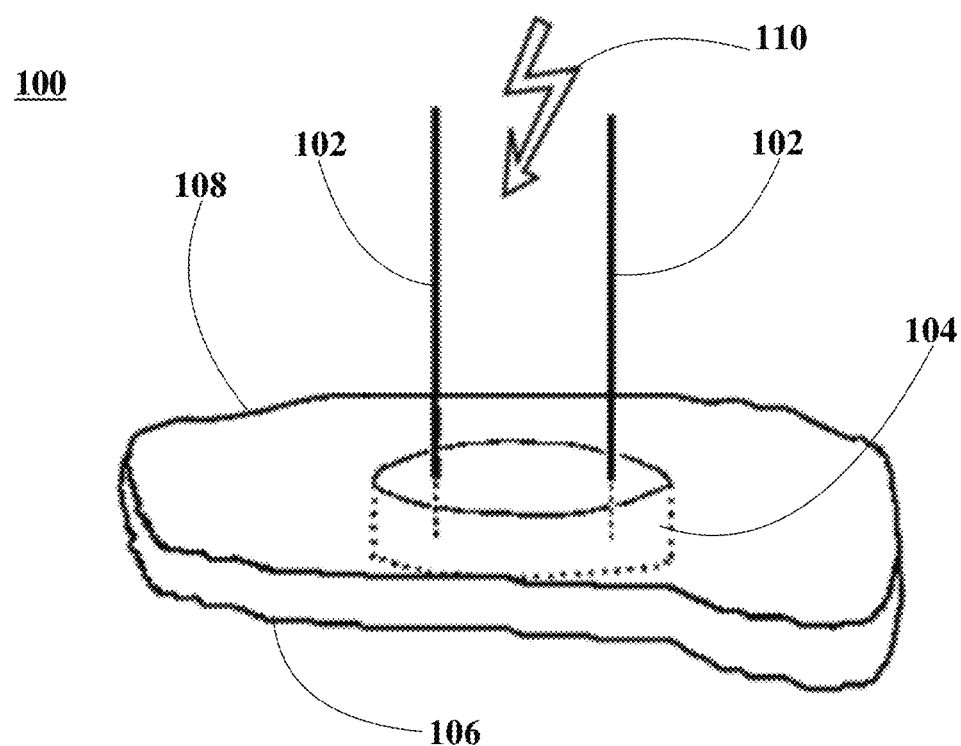
FIG. 1 is a graphical representation illustrating a penetrating configuration of electrodes for ablating myocardial tissue using a method of ablation with nanosecond pulsed electric fields (nsPEFs), according to an embodiment.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the disclosure. One having ordinary skill in the relevant art, however, will readily recognize that the embodiments of the disclosure can be practiced without one or more of the specific details or with other methods. In other instances, well-known structures or operations are not shown in detail to avoid obscuring the aspects of the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

Definitions

As used here, the following terms have the following definitions:

"Nanosecond pulsed electric fields (nsPEFs)" refers to electric pulses of nanosecond duration.

"Cardiac tissue" refers to the tissue of the heart.

"Transmural lesion" refers to a scar tissue that extends all the way from surface to opposing surface in a cardiac wall (e.g. epicardium to endocardium).

"Myocardial ablation" refers to a procedure that can correct heart rhythm problems (e.g., arrhythmias) by scarring or removing portions of cardiac tissue that trigger abnormal heart rhythm.

"Electroporation or electroporated" refers to a physical method that uses an electrical pulse to create temporary pores in cell membranes, thus inducing necrosis or apoptosis on the electroporated cells.

"Electrode" refers to a conducting material configured for the application of a charge, voltage, and/or electric field to myocardial tissue.

"Pulser circuit" refers to a circuit that generates and delivers very short and intense nsPEFs to electrodes.

"Arrhythmia" refers to a problem with the rate or the rhythm of the heartbeat.

"Atrial fibrillation or AF" refers to an arrhythmia characterized by fast and irregular activation of the atria.

"Ablation uniformity" refers to how evenly all cells within the tissue are electroporated.

"nsPEF ablation" refers to the ablation of myocardial tissue using nanosecond pulsed electric fields.

"Langendorff setup" refers to a predominant in vitro technique used in pharmacological and physiological research using isolated animal hearts, allowing the examination of cardiac contractile strength and heart rate without the complications of an intact animal.

"Non-conducting lesion" refers to ablated lesion tissue that disrupts the abnormal electrical pathway(s).

DESCRIPTION OF THE DRAWINGS

In view of the limitations of existing ablation methods, the various embodiments in the present disclosure are directed to new methods to ablate cardiac tissue using nanosecond pulsed electric fields (nsPEFs).

The electric pulses used to generate nsPEFs can have a pulse duration from about 1 ns to about 1,000 ns with amplitudes from about 1 kV to about 100 kV. Because the pulses are so short, the energy deposited is quite low and the mode of action is non-thermal. This means that the most severe side effects of RF ablation in the form of heat-induced thrombus formation, steam pops, and damage to adjacent tissues are avoided.

In some embodiments ablation of myocardial tissues can be done with a short burst of shocks where the total ablation time is negligible (~1 second). In RF and cryoablation, ablation times generally range between about 10 seconds and about a minute per application site. Therefore, current ablation procedures take from about 2 hours to about 4 hrs in total. In these embodiments of new methods of ablation using nsPEF, the total time per procedure can be reduced to about 75% of total time used by other ablation methods.

Electrode Configurations

In view of the limitations of existing ablation systems and methods, some embodiments in the present disclosure are directed to new systems and methods to ablate cardiac tissue using nanosecond pulsed electric fields (nsPEFs).

According to some embodiments, electric pulses used to generate nsPEFs can have a pulse duration from about 1 ns to about 1,000 ns with amplitudes from about 1 kV to about 100 kV. Because the pulses are so short, the energy delivered is low enough so that the mode of action is non-thermal. In other words, the most severe side effects of RF ablation in the form of heat-induced thrombus formation, steam pops, and damage to adjacent tissues are avoided.

In some embodiments, ablation of myocardial tissues can be performed with a short burst of energy where the total ablation time is negligible. In RF and cryoablation, ablation times generally range from about 10 seconds to about a minute per application site. Therefore, current ablation procedures can take from 2 hours to 4 hours. In these embodiments of the methods of ablation using nsPEF, the total time per procedure can be reduced about 75% of the total time used by other ablation methods.

Electrode Configurations

The nanosecond pulsed electric field ablation of the various embodiments can be performed using any of three different electrodes configurations, each of which has specific advantages.

FIG. 1 is a graphical representation illustrating a penetrating configuration of electrodes for ablating myocardial tissue using a method of ablation with nanosecond pulsed electric fields (nsPEFs), according to an embodiment.

In FIG. 1, penetrating electrode configuration 100 includes two thin parallel shock electrodes 102, ablated tissue volume 104, epicardium 106, endocardium 108, and pulser circuit 110. In FIG. 1, electrodes 102 are inserted into the tissue, such as, all the way through the tissue wall. In other embodiments, penetrating electrode configuration 100 can further include a supporting member, where the first and second electrodes 102 co-extend from the supporting member substantially in parallel. In these embodiments, each of a first distal end of the first electrode and a second distal end of the second electrode can include a contact area. In other embodiments, the penetrating electrode configuration includes a catheter that has retractable electrodes. Penetrating electrode configuration 100 can include more components, less components, or differently arranged components than those illustrated in FIG. 1.

In FIG. 1, the electric field applied to the tissue is the same at all depths in the tissue. This leads to approximately equal amount of tissue being ablated in all depths of the tissue, and an approximate cylindrical shape of ablated tissue volume 104, which exhibits an elliptical cross section. The consistent electric field applied by pulser circuit 110 reduces the amount of tissue that needs to be ablated significantly. The reduction in the amount of tissue is due to the requirement that lesions must be non-conducting tissue and when ablated using the penetrating configuration of electrodes the result is a consistent minimal width that provides the required non-conducting tissue barrier. The cross section of ellipsoidal ablation volumes is much smaller at epicardium 106 than at endocardium 108, but even at the epicardium, the ablated tissue still needs to be a minimum required size, for example, about 5 mm wide. In other words, much more tissue has to be ablated closer to the endocardium.

In some embodiments, penetrating electrode configuration 100 can use a plurality of pulser circuits 110 as known in the art, which can provide high-amplitude rectangular electric pulses of nanosecond duration, such as a pulsed forming line (PFL) circuit.

Figure 2:
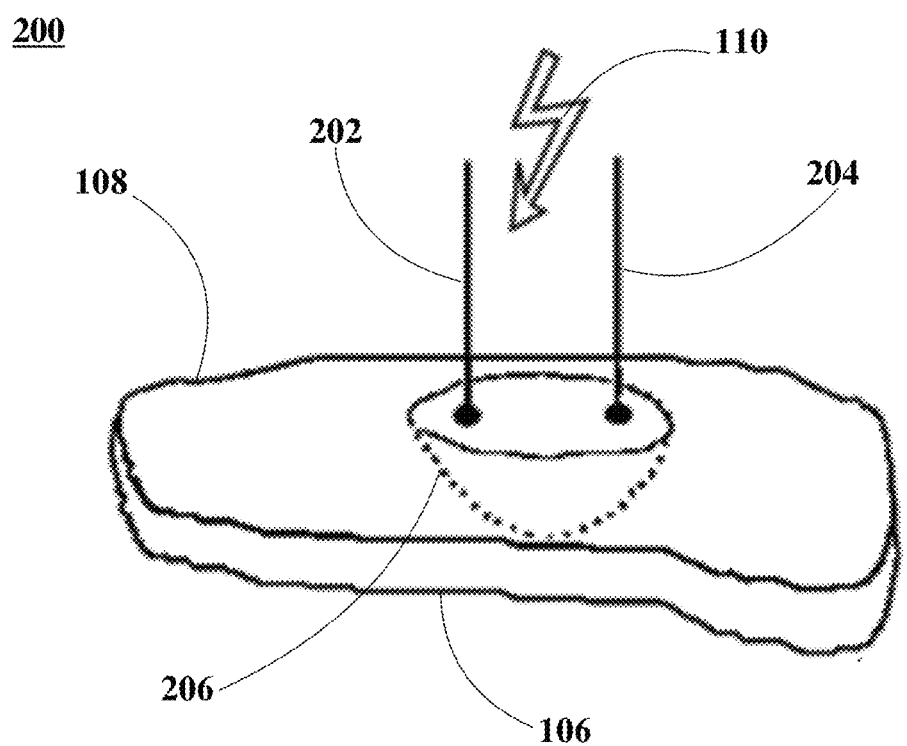
FIG. 2 is a graphical representation illustrating an endo-endo configuration of electrodes for ablating myocardial tissue using a method of ablation with nsPEFs, according to an embodiment.

FIG. 2 is a graphical representation illustrating an endo-endo configuration of electrodes for ablating myocardial tissue using a method of ablation with nanosecond pulsed electric fields (nsPEF), according to an embodiment.

In FIG. 2, endo-endo electrode configuration 200 includes epicardium 106, endocardium 108, pulser circuit 110, first electrode 202, second electrode 204, and ellipsoidal ablation volume 206. In some embodiments, first electrode 202 is located on a first surface of endocardium 108 and second electrode 204 is located on a second surface of endocardium 108, such as, for example adjacent to the first surface location. In these embodiments, first electrode 202 and second electrode 204 are placed so as to be in substantially parallel orientation. Further to these embodiments, each of a first distal end of the first electrode and a second distal end of the second electrode can include a contact area. Endo-endo electrode configuration 200 is the most straightforward to implement; existing RF ablation catheters can be used with small modifications. Endo-endo electrode configuration 200 can include more components, less components, or differently arranged components than those illustrated in FIG. 2.

In FIG. 2, first electrode 202 and second electrodes 204 are implemented as shock electrodes and both touch, but do not penetrate the surface of endocardium 108. In some embodiments, the nsPEFs applied to myocardial tissue results in ellipsoidal ablation volume 206 and reduced thermal side effects. The speed of application of nsPEFs allows a reduction in the procedure time, for example, of about 75% of current procedures and the procedures total ablation time can be considered negligible (<<1 second). Endo-endo electrode configuration 200 does not require tissue penetration to perform nsPEF ablation of myocardial tissue.

Endo-endo electrode configuration 200 can use a plurality of pulser circuits 110 as known in the art, which can provide high-amplitude rectangular electric pulses of nanosecond duration, such as a pulsed forming line (PFL) circuit.

Figure 3:
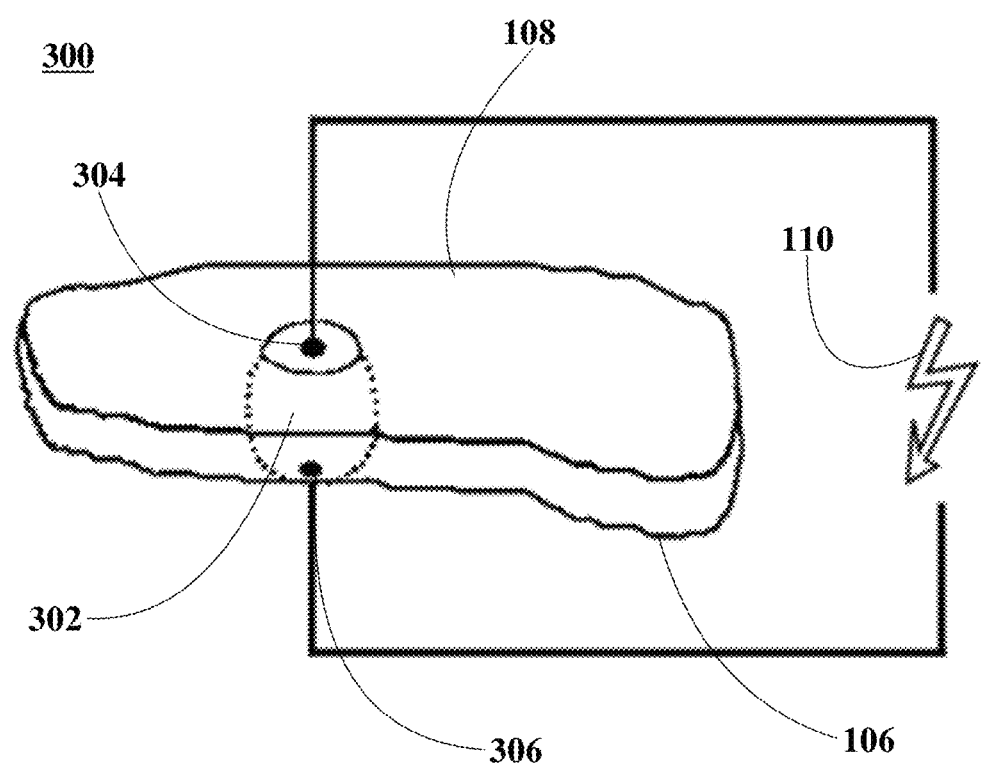
FIG. 3 is a graphical representation illustrating an endo-epi configuration of electrodes for ablating myocardial tissue using a method of ablation with nsPEFs, according to an embodiment.

FIG. 3 is a graphical representation illustrating an endo-epi configuration of electrodes for ablating myocardial tissue using a method of ablation with nanosecond pulsed electric fields (nsPEFs), according to an embodiment.

In FIG. 3, endo-epi electrode configuration 300 includes epicardium 106, endocardium 108, pulser circuit 110, ablated volume 302, first electrode 304, and second electrode 306. In some embodiments, first electrode 304 is located on a surface of endocardium 108 and second electrode 306 is located on a surface of epicardium 106, where the location associated with second electrode 306 is on the surface of epicardium 106 substantially opposite to the location of the first electrode 304 located on the surface of endocardium 108. In other words, first electrode 304 and second electrode 306 are placed so that they extend substantially collinearly. In these embodiments, each of a first distal end of the first electrode and a second distal end of the second electrode can include a contact area. Endo-epi electrode configuration 300 can include more components, less components, or differently arranged components than those illustrated in FIG. 3.

In some embodiments, endo-epi electrode configuration 300 produces nsPEFs that are substantially equal at all tissue depths. In these embodiments, endo-epi electrode configuration 300 produces results that are substantially similar to the penetrating electrode configuration, as described in FIG. 1, in terms of the quality of the geometry of ablated volume 302. In FIG. 3, endo-epi electrode configuration 300 does not require tissue penetration and existing catheters can be used with minimal modifications. However, this configuration requires one endocardial catheter and one endothoracic catheter.

Endo-epi electrode configuration 300 can use a plurality of pulser circuits 110 as known in the art, which can provide high-amplitude rectangular electric pulses of nanosecond duration, such as a pulsed forming line (PFL) circuit.

Electrode Materials

In the embodiments for nsPEF ablation of myocardial tissue described in FIGS. 1-3, the electrodes are conductive, rigid, and thin, for ease of insertion and to limit tissue damage. For example, tungsten or tungsten carbide can be used for penetrating electrodes due to tungsten's extraordinary rigidity and because adverse effects have not been detected at the interface of electrode and tissue. However, these embodiments are not limited in this regard. Therefore, other rigid conductor materials can be used, for example tungsten carbide, steel alloys, or titanium, amongst others.

The electrode diameters can vary according to the application. However, diameters as low as about 250 µm are relatively easy to insert and can be used to produce sufficient currents for ablating myocardial tissue.

Electrode Designs

In general, it is desirable to keep the diameter (a) of penetrating electrodes small, for easy insertion and to limit tissue damage. In some embodiments, an electrode diameter (a) of about 250 µm can produce little to no significant tissue damage in addition to allowing easy insertion as thinner electrodes do not enter the tissue at a substantially perpendicular angle. Conversely, thicker electrodes are hard to insert and may damage tissue. Accordingly, the present disclosure contemplates a range of diameters (a) from about 100 µm to about 1,000 µm, depending on the electrode materials. For example, in the case of tungsten the range of diameters (a) can range from about 125 µm to about 500 µm. These configurations of electrodes can provide effective delivery of shocks to the desired tissue locations.

Figure 4:
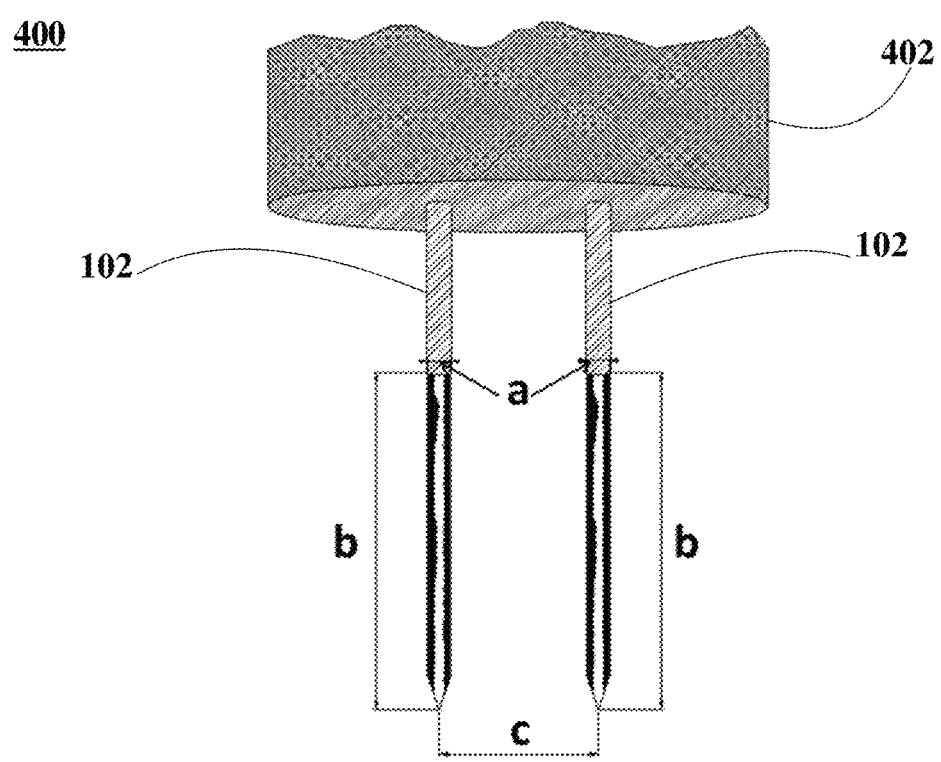
FIG. 4 is a graphical representation illustrating a design of electrodes for a penetrating electrode configuration, according to an embodiment.

FIG. 4 is a graphical representation illustrating a design for penetrating electrodes as described in FIG. 1, according to an embodiment. In FIG. 4, penetrating electrode configuration 400 includes penetrating electrodes 102 and housing 402. Penetrating electrode configuration 400 can include more components, less components, or differently arranged components than those illustrated in FIG. 4.

In FIG. 4, penetrating electrodes 102 coextend from housing 402 and are substantially parallel to one another. In some embodiments, the distance between the electrodes determines the size of the ablated volume of tissue created by the application of nsPEFs. In these embodiments, a variety of inter-electrode distances can be utilized.

In some embodiments, an electrode with a spacing (c) of about 2 mm that is paired with appropriate nsPEFs can consistently create ablated volumes with a width from about 4 mm to about 6 mm, which is typically the desired width of non-conducting lesions. If in special cardiological circumstances wider lesions should be desired, the ablated volumes can also be created by choosing an electrode spacing greater than 4 mm.

In some embodiments, the length (b) of the electrodes reflects the thickness of the tissue that needs to be penetrated. Generally, the right atrium thickness of the human heart is from about 2 mm to about 4 mm and the left atrium thickness of the human heart is about 4 mm. When the thicknesses of the ventricles are considered, electrodes from about 6 mm to about 12 mm in length (b) can be used.

As seen in FIG. 4, electrodes 102 are round with conical ends. However, the various embodiments for the configurations of the electrodes in the present disclosure, including configurations that allow easy insertion, are not limited by the shape of the electrodes and their ends. Neither are the various embodiments for the configurations of the electrodes limited by the length (b) of the electrodes, such that different lengths can be used.

Figure 5:
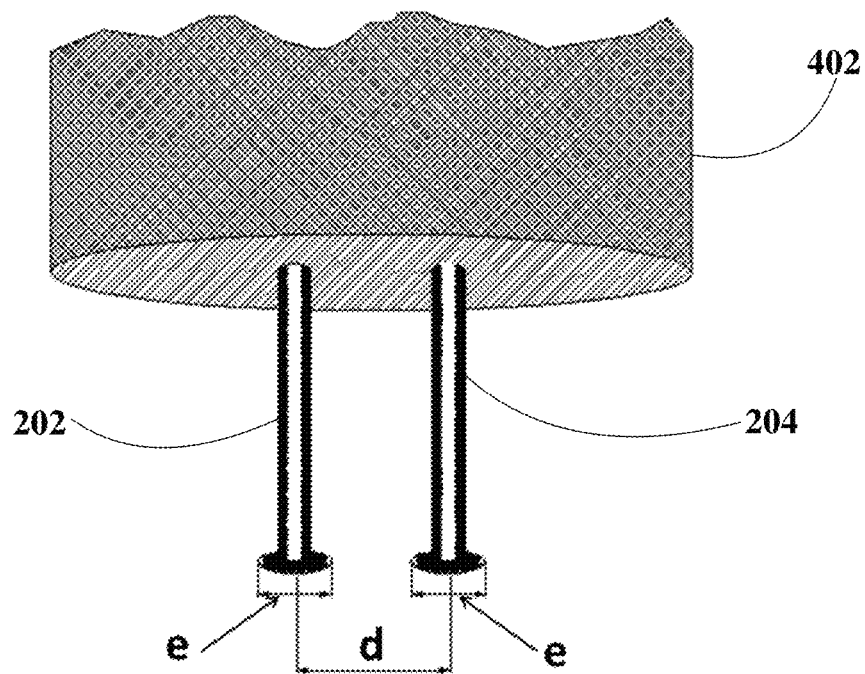
FIG. 5 is a graphical representation illustrating a design of electrodes for an endo-endo electrode configuration, according to an embodiment.

FIG. 5 is a graphical representation illustrating a design for endo-endo electrodes as described in FIG. 2, according to an embodiment. In FIG. 5, endo-endo electrode configuration 500 includes first electrode 202, second electrode 204, and housing 402. Endo-endo electrode configuration 500 can include more components, less components, or differently arranged components than those illustrated in FIG. 5.

In FIG. 5, First electrode 202 and second electrode 204 coextend from housing 402 in a substantially parallel orientation. Further, first electrode 202 and second electrode 204 do not need to penetrate tissue so rigidity is less of a concern. In some embodiments, less rigid materials as opposed to materials used for penetrating electrodes, can be used for the manufacture of electrodes to be used in endo-endo electrode configuration 500. In these embodiments, platinum-iridium is useful as the contact material because it is particularly non-reactive and non-toxic as well as resistant to dissolution. However, the various embodiments for the configurations in the present disclosure are not limited in this regard and other common electrode materials, such as silver and stainless steel amongst others, can also be used.

In some embodiments, a contact area can be provided at distal ends of first electrode 202 and second electrode 204. In these embodiments, the contact area can be enlarged with respect to the thickness of the electrodes to improve contact with the underlying tissues. In other embodiments, the contact regions can be substantially planar. In these embodiments, the ends can be rounded or otherwise concave to improve contact with the underlying tissues. In one particular embodiment, as illustrated in FIG. 5, the contact areas can be circular and substantially planar. In this embodiment, first electrode 202 and second electrode 204 have a diameter (e) of from about 4 mm to about 6 mm and can be spaced (d) from about 2 mm apart to about 4 mm apart, so that there is a gap of about 2 mm between the contact areas. Further to this embodiment, this endo-endo electrode configuration can create ablated volumes with a width from about 4 mm to about 6 mm.

Although FIG. 5 shows round electrodes with circular contact areas, the various embodiments in the present disclosure are not limited in this regard and other configurations can be used, including different shapes for the electrodes and the contact areas.

Figure 6:
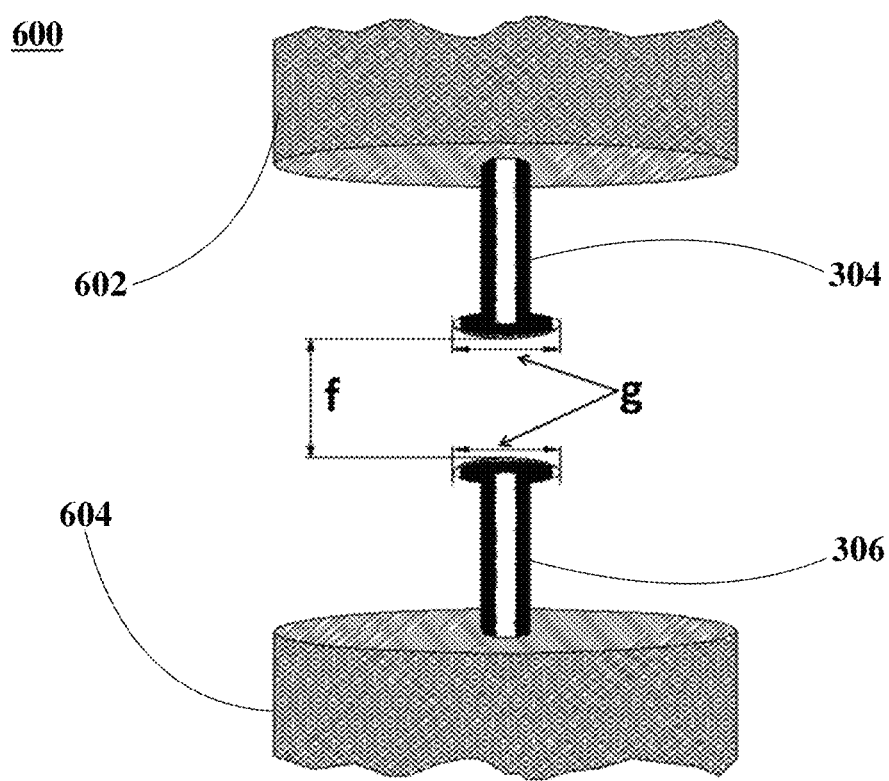
FIG. 6 is a graphical representation illustrating a design of electrodes for a first endo-epi electrode configuration, according to an embodiment.

FIG. 6 is a graphical representation illustrating a design for endo-epi electrodes, as described in FIG. 3, according to an embodiment. In FIG. 6, endo-epi electrode configuration 600 includes first electrode 304, second electrode 306, and housings 602 and 604. In FIG. 6, first electrode 304 is associated with housing 602 and second electrode 306 is associated with housing 604. Endo-epi electrode configuration 600 can include more components, less components, or differently arranged components than those illustrated in FIG. 6.

In some embodiments, first electrode 304 and second electrode 306 extend substantially collinearly from their respective housing 602 and 604 and do not penetrate tissue. In these embodiments, first electrode 304 and second electrode 306 can be configured substantially similarly to those electrodes in endo-endo electrode configuration 500 as described in FIG. 5, above. In other embodiments and as illustrated in FIG. 6, the circular contact areas have a diameter (g) of from about 3 mm to about 6 mm and the spacing (f) is equivalent to the thickness of the cardiac wall (e.g. 4 mm for a human atrium). In these embodiments, this configuration creates ablated volumes with widths from about 3 mm to about 6 mm.

Although FIG. 6 shows round electrodes with circular contact areas, the various embodiments in the present disclosure are not limited in this regard and other configurations can be used, including different shapes for the electrodes and the contact areas.

In some embodiments, lesions can be created using single ablation techniques. In other embodiments, different combinations of single ablation techniques can be used to create a non-conducting lesion.

FIG. 7 is a graphical representation illustrating methods of combining single ablations to yield a least one lesion on myocardial tissue using either the penetrating electrode configuration or the endo-endo electrode configuration and incorporating nsPEFs, according to some embodiments. In FIG. 7, lesions are created by single ablation applications in the form of semicircles representing the electrode positions at the end points of each semicircle.

Figure 7A:
FIG. 7A is a graphical representation illustrating the anticipated result of the side-by-side lesion methodology implemented using either the penetrating electrode configuration or the endo-endo electrode configuration and incorporating nsPEFs, according to an embodiment.

FIG. 7A is a graphical representation illustrating the anticipated result of the side-by-side lesion methodology implemented using either the penetrating electrode configuration or the endo-endo electrode configuration and incorporating nsPEFs, according to an embodiment.

In FIG. 7A, side-by-side lesion method 702 requires both electrodes be placed outside the previously ablated volume, leading to minimal overlap of the ablated volume. In some embodiments, side-by-side lesion method 702 is the fastest of the three disclosed methods to ablate tissue and produce non-conducting lesions. Further to this embodiment, side-by-side lesion method 702 provides lesion widths that vary within an acceptable range from about 4 mm to about 6 mm.

Figure 7B:
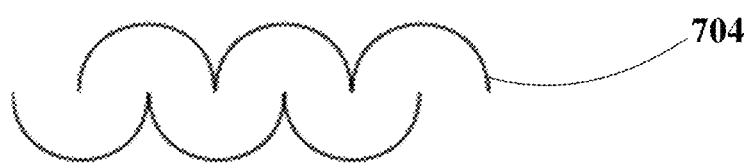
FIG. 7B is a graphical representation illustrating the anticipated result of the interwoven lesion methodology implemented using either the penetrating electrode configuration or the endo-endo electrode configuration and incorporating nsPEFs, according to an embodiment.

FIG. 7B is a graphical representation illustrating the anticipated result of the interwoven lesion methodology implemented using either the penetrating electrode configuration or the endo-endo electrode configuration and incorporating nsPEFs, according to an embodiment.

In FIG. 7B, interwoven lesion method 704 requires the placement of one of the electrodes approximately in the center of the ablated volume produced by the previous ablation application. In these embodiments, interwoven lesion method 704 provides a more uniform lesion thickness, but the ablation process requires about twice the time as side-by-side lesion method 702.

Figure 7C:
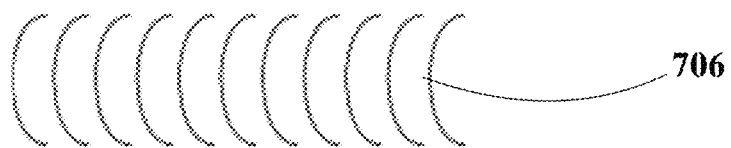
FIG. 7C is a graphical representation illustrating the anticipated result of the sideways lesion methodology implemented using either the penetrating electrode configuration or the endo-endo electrode configuration and incorporating nsPEFs, according to an embodiment.

FIG. 7C is a graphical representation illustrating the anticipated result of the sideways lesion methodology implemented using either the penetrating electrode configuration or the endo-endo electrode configuration and incorporating nsPEFs, according to an embodiment.

In FIG. 7C, sideways lesion method 706 is performed by relocating the electrodes after each shock application in the direction of the short axis of the ablated volume. In some embodiments, sideways lesion method 706 is the most time-consuming method, but sideways lesion method 706 can provide non-conducting lesions with the most homogeneous widths.

EXAMPLES

The following examples and results are presented solely for illustrating the various embodiments in the present disclosure and are not intended to limit the various embodiments in any way.

For these examples, four New Zealand rabbit hearts were isolated and placed in a Langendorff setup. Then, optical mapping was used to establish a control activation map during myocardial surface stimulation. Two shock electrodes were repeatedly inserted, spaced 25 mm apart, into the left ventricle through the entire wall. For the mapping of the heart about 50 pulses at about 1 Hz each were applied to electrodes using an intensity of about 0.52 kV/mm for about 300 ns. Additionally, propidium iodide stains were used to characterize the geometry of the ablated volume.

Figure 8:
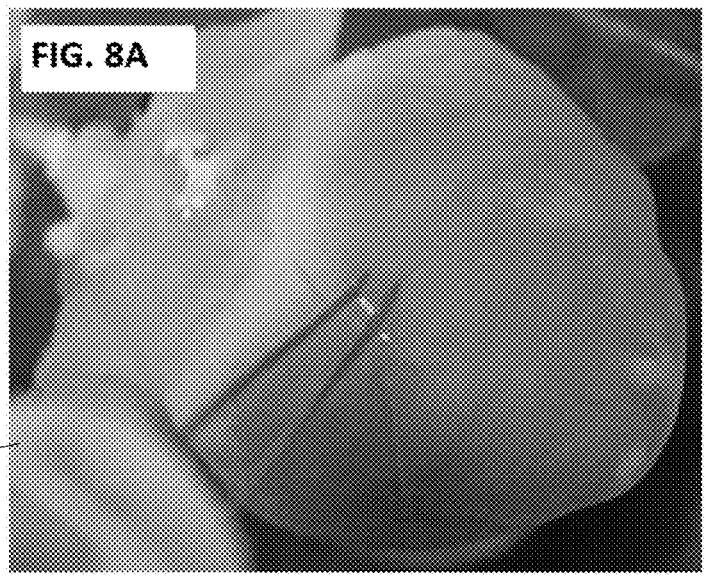
FIG. 8 includes photographic representations depicting a pulse application using a penetrating electrode configuration for ablation of myocardial tissue and incorporating nsPEFs, according to some embodiments.
Figure 8:
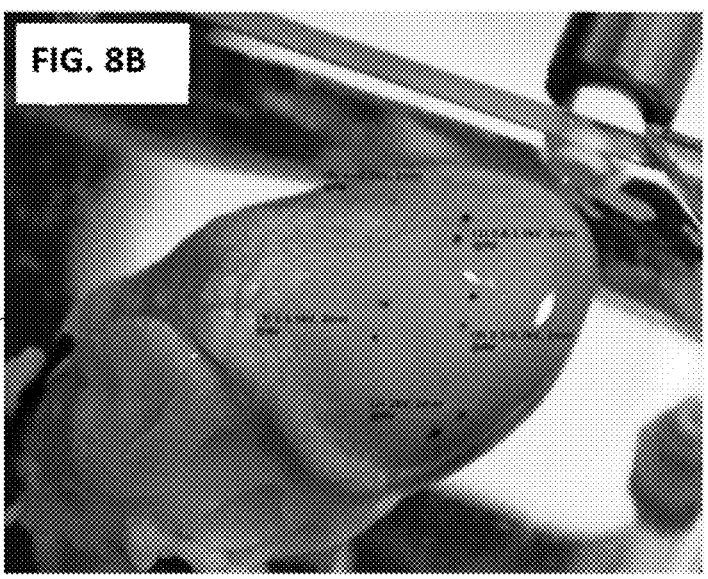

FIG. 8 includes photographic representations depicting a pulse application using a penetrating electrode configuration for ablation of myocardial tissue and incorporating nsPEFs, according to various embodiments.

FIG. 8A is a photographic representation depicting pulse application 802 using a penetrating electrode configuration implemented with tungsten wires to create lesions within heart ventricle tissue and incorporating nsPEFs, according to an embodiment.

FIG. 8B is a photographic representation depicting a layout of electrode planned positions 804 marked with surgical ink, using a penetrating electrode configuration incorporating nsPEFs to create lesions within heart ventricle tissue, according to an embodiment.

As shown in FIG. 8A, two 250 µm tungsten wires, spaced from about 2 mm to about 5 mm in a substantially parallel orientation, are used to apply shocks. In some embodiments, the 250 μm tungsten wires are used to create multiple lesions on each of the ventricles. In FIG. 8B, the planned electrode positions are marked with surgical ink.

Figure 9:
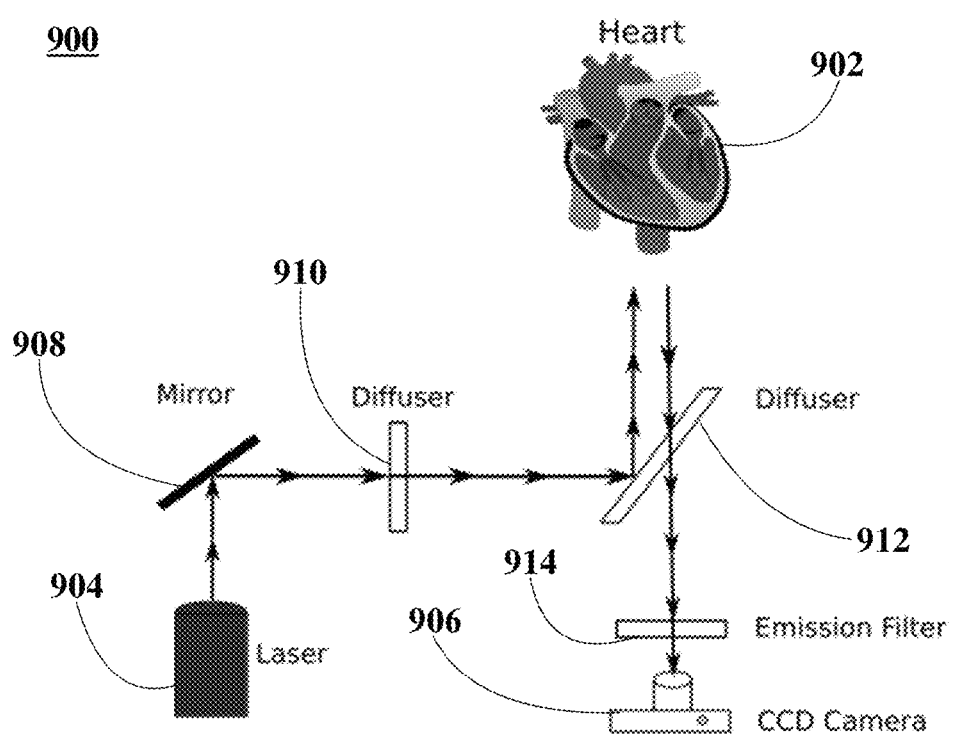
FIG. 9 is a graphical representation illustrating a system for an optical mapping of the heart.

FIG. 9 is a graphical representation illustrating a system for optical mapping of the heart, according to an embodiment.

In some embodiments, Langendorff-perfused hearts 902 are loaded with the voltage-sensitive fluorescent probe Di-4-ANBDQBS (about 150 nmol per gram of tissue) and the electromechanical uncoupler blebbistatin inhibitor (about 5 μM to about 10 μM continuous). Then, each heart is illuminated with about 671 nm laser light from laser source 904. In some embodiments, a 715 nm fluorescent light level is recorded with a suitable charge-coupled device (CCD) camera 906, such as the CCD camera model Little Joe available from SciMeasure Analytical Systems, Inc. The setup for the optical mapping of the heart includes a mirror 908, diffusers 910 and 912, and emission filter 914, as seen in FIG. 9.

Figure 10:
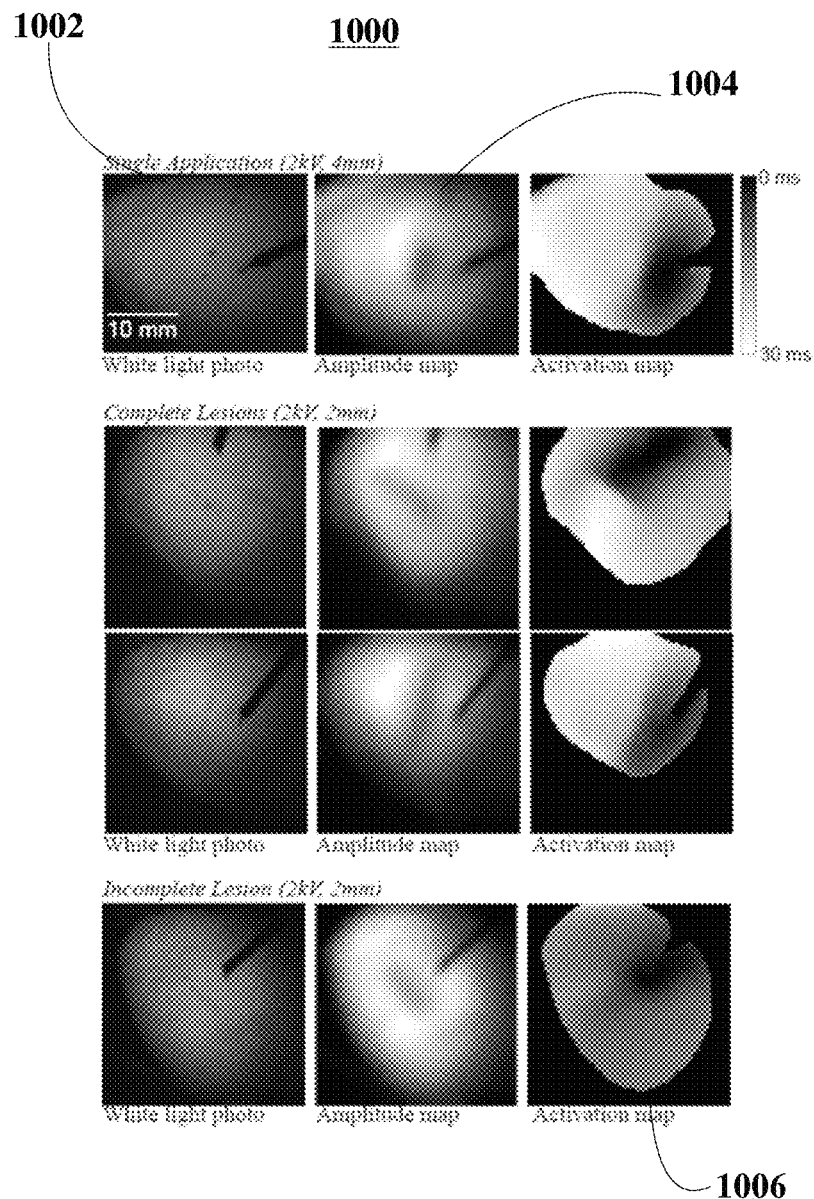
FIG. 10 is a photographic representation depicting an electrophysiological analysis of lesions created using a pulse application implementing a penetrating electrode configuration and incorporating nsPEFs, according to an embodiment.

FIG. 10 is a photographic representation depicting an electrophysiological analysis of lesions created using a pulse application implementing a penetrating electrode configuration and incorporating nsPEFs, according to an embodiment.

In FIG. 10, an electrophysiological analysis of the resulting lesions as filmed using an optical mapping technique, such as, for example the optical mapping technique described in FIG. 9, above. In FIG. 10, the resulting pictures include single, complete, and incomplete lesions, as seen in column 1002 of white light photos. Column 1004 shows an amplitude map for each type of lesions, and column 1006 depicts an activation map for same type of lesions.

In FIG. 10, the white light photos of column 1002 are ordinary photographs to illustrate the setup used for the results described herein. The cardiac surface appears medium gray and fills most of the figure. The small black dots mark the insertion sites of the shock electrodes. The larger elongated black shadow is from the stimulation electrode.

In FIG. 10, the amplitude maps of column 1004 illustrates color-coded action potential amplitudes determined using optical mapping during stimulation of the heart. White pixels correspond to large action potential amplitudes and dark pixels correspond to low action potential amplitudes. The amplitude maps of column 1004 illustrate that between the insertion sites of the shock electrodes the action potential amplitude has dropped sharply, because the tissue there has been ablated.

In FIG. 10, the activation map of column 1006 illustrates the sequences of electrical activation during stimulation determined using optical mapping. Black pixels indicate early activation and white pixels indicate late activation. The activation map also shows that after the successful creation of a lesion, the propagation of activation is blocked at the lesion. This is particularly apparent in the first example of a successful lesion, in which the central upper part of the heart, close to the stimulation electrode, is quickly activated. Activation stalls and the lower parts of the heart are only activated after excitation has propagated around the ablated tissue. This block at the lesion leads to a sharp transition from dark to bright at the lesion, because the activation times on both sides of the lesion differ greatly.

Figure 11:
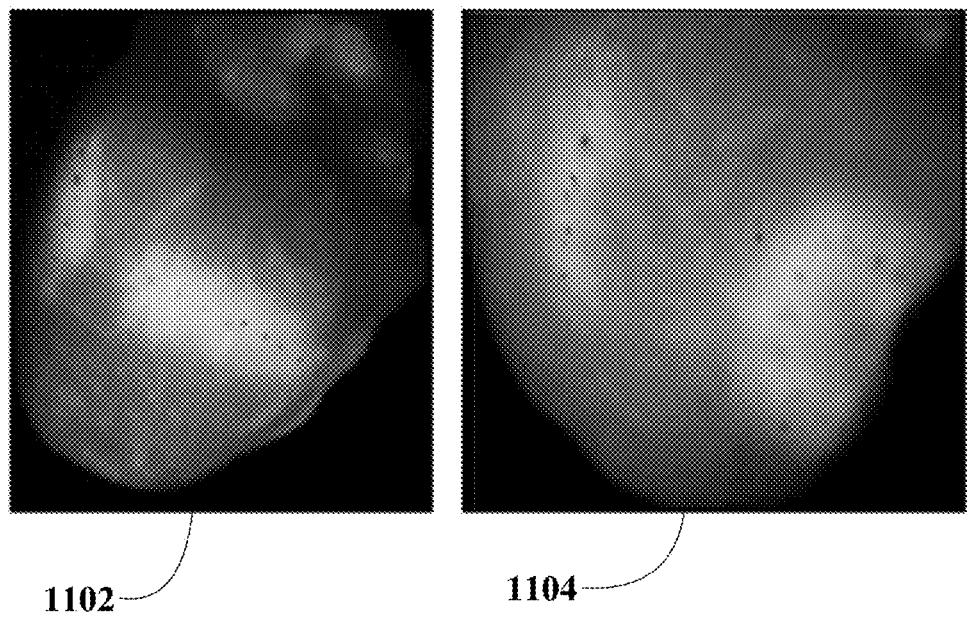
FIG. 11 is a photographic representation depicting a propidium iodide fluorescence analysis of lesions created using a pulse application implementing a penetrating electrode configuration and incorporating nsPEFs, according to an embodiment.

FIG. 11 is a photographic representation depicting a propidium iodide fluorescence analysis of lesions created using a pulse application implementing a penetrating electrode configuration and incorporating nsPEFs, according to an embodiment.

In FIG. 11, propidium iodide fluorescence analysis 1100 includes views 1102 and 1104. In some embodiments, the geometry of the ablated volume is determined using propidium iodide staining. In these embodiments, propidium iodide enters dead cells only and binds to the deceased cells' DNA. In these embodiments, propidium iodide fluorescence can be used to identify the dead parts of a tissue. In FIG. 11, views 1102 and 1104 illustrate dead tissue as the lighter colored portions of the cardiac tissue.

In an example and referring to views 1102 and 1104, Langendorff-perfused hearts are loaded with propidium iodide for about 30 minutes with about 30 minutes washout. Fluorescence is excited with about 532 nm laser light, and the fluorescent light is isolated using a 550 nm long pass filter and recorded with a CCD camera. FIG. 11 clearly shows that the surface tissue around the electrode insertion sites is successfully ablated.

Figure 12:
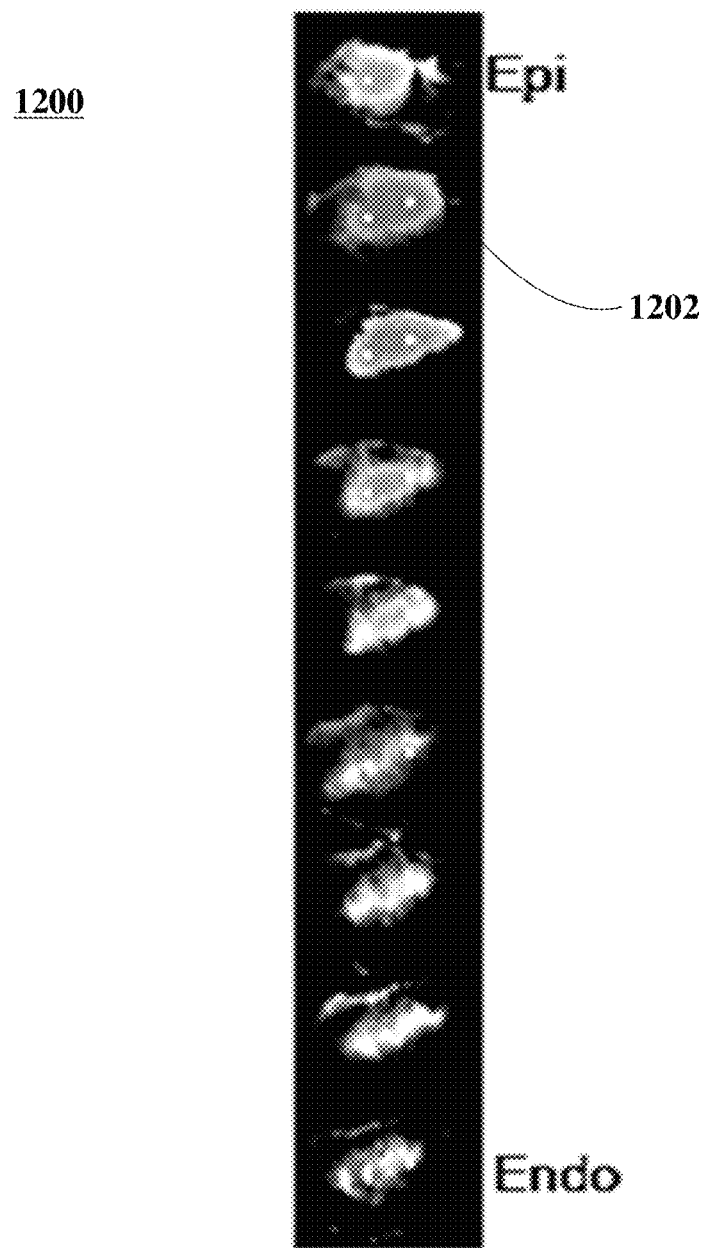
FIG. 12 is a photographic representation depicting the method of tridimensional (3D) reconstruction of lesions created using a single pulse application implementing a penetrating electrode configuration and incorporating nsPEFs, according to an embodiment.

FIG. 12 is a photographic representation depicting the method of tridimensional (3D) reconstructions of lesions created using a single pulse application implementing a penetrating electrode configuration and incorporating nsPEFs, according to an embodiment.

In FIG. 12, 3D reconstruction of lesions for a single pulse application is obtained. In some embodiments, the lesion is excised and sectioned in about 300 μm thin slices 1202. In these embodiments, for each slice 1202, the sequence of nine pictures (arranged vertically, "epi" to "endo" and as seen in FIG. 12) shows the ablated tissue in each of nine sections of tissue thickness of about 2.5 mm. Further to these embodiments, the lighter colored portions of the cardiac tissue illustrate ablated tissue.

FIG. 13 includes graphical representations illustrating 3D reconstructions of lesions created using a single pulse application and multiple pulse applications that are implemented using a penetrating electrode configuration that incorporates nsPEFs, according to various embodiments.

FIG. 13A is a graphical representation depicting a 3D reconstruction of a lesion 1302 created using a single pulse application implementing a penetrating electrode configuration and incorporating nsPEFs, according to an embodiment.

FIG. 13B is a graphical representation depicting a 3D reconstruction of lesions 1304 created using multiple pulse applications implementing a penetrating electrode configuration and incorporating nsPEFs, according to an embodiment.

FIG. 13 illustrates a reconstruction of an entire ablated volume from individual sections. In FIG. 13B, the two larger three-dimensional renderings show different views of a larger lesion (created in the same way as the rendering of the smaller lesion in FIG. 13A). FIG. 13 illustrates that ablation is successful throughout the entire thickness of the cardiac wall and that the cross sections of the ablated volume are relatively constant from endocardium to epicardium. Additionally, these embodiments illustrate that the disclosed nsPEF ablation methods allow for the reduction of ablated tissue while maintaining a necessary thickness of the lesions.

Table 1 below details lesion success rates and includes lesion widths for different shock parameters using single and multiple pulse applications and implementing nsPEF ablation of myocardial tissue.

TABLE 1

Approximate Success Rates for Completed Lesions

| Shock Parameters | Lesion Width [mm] | Success Rate |
|---|---|---|
| 1 kV, 2.3 mm, 300 ns, 50 pulses | 2-3 | >70% |
| 2 kV, 2.3 mm, 300 ns, 50 pulses | 3-4 | ~100% |
| 4 kV, 2.3 mm, 300 ns, 50 pulses | 4-5 | ~100% |
| 2 kV, 4 mm, 300 ns, 50 pulses | 3-4 | >90% |
| 4 kV, 4 mm, 300 ns, 50 pulses | 4-6 | ~100% |
| 2.3 kV, 2.3 mm, 300 ns, 5 pulses | 3-4 | ~100% |
| 4.5 kV, 2.3 mm, 300 ns, 5 pulses | 4-5 | ~100% |

The foregoing illustrates how non-conducting lesions can be created using nsPEFs, in accordance with the various embodiments in the present disclosure. Under controlled conditions, a stimulus applied to the myocardial surface initiates a wave of electrical activation that propagates in all directions. After a lesion has been created by inserting the electrode pair and applying nsPEFs, the activation map shows a clear line of block. The width of the lesions can be controlled via the electrode spacing and the shock parameters. Ablation with nsPEFs does not significantly heat tissue, so thermal damage to neighboring tissues does not occur. Therefore, ablation using nsPEFs is an alternative to RF ablation for atrial fibrillation. Ablation using nsPEFs can also reduce the amount of lost atrial tissue and reduce the risk for serious complications.

While various embodiments of the present disclosure have been described above, it should be understood that they have been presented by way of example only, and not limitation. Numerous changes to the disclosed embodiments can be made in accordance with the disclosure herein without departing from the spirit or scope of the disclosure. Thus, the breadth and scope of the present disclosure should not be limited by any of the above described embodiments.

Rather, the scope of the disclosure should be defined in accordance with the following claims and their equivalents.

Although the present disclosure has been illustrated and described with respect to one or more implementations, equivalent alterations and modifications can occur to others skilled in the art upon the reading and understanding of this specification and the drawings. In addition, while a particular feature of the disclosure may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

REFERENCES

The following references describe certain aspects of the various embodiments and are all herein incorporated by reference in their entirety:

[1] Latchamsetty, R. & Oral, H. Ablation of atrial fibrillation using an irrigated-tip catheter: open or closed? Pacing Clin. Electrophysiol. 35, 503-505 (2012).
[2] Naccarelli G V, Varker H, Lin J, Schulman K L. Increasing prevalence of atrial fibrillation and flutter in the United States. Am J Cardiol 2009; 104:1534-9. doi:10.1016/j.amjcard.2009.07.022.
[3] Roger V L, Go A S, Lloyd-Jones D M, Adams R J, Berry J D, Brown T M, et al. Heart disease and stroke statistics—2011 update: a report from the American Heart Association. Circulation 2011; 123:e18-209. doi: 10.1161/CIR.0b013e3182009701.
[4] Marini C, Santis F D, Sacco S, Russo T, Olivieri L, Totaro R, et al. Contribution of Atrial Fibrillation to Incidence and Outcome of Ischemic Stroke Results From a Population-Based Study. Stroke 2005; 36:1115-9. doi:10.1161/01.STR.0000166053.83476.4a.
[5] Go A S H E. Prevalence of diagnosed atrial fibrillation in adults: National implications for rhythm management and stroke prevention: the anticoagulation and risk factors in atrial fibrillation (atria) study. JAMA 2001; 285:2370-5. doi:10.1001/jama.285.18.2370.
[6] Thrall G, Lane D, Carroll D, Lip G Y H. Quality of Life in Patients with Atrial Fibrillation: A Systematic Review. Am J Med 2006; 119:448.e1-448.e19. doi: 10.1016/j.amjmed.2005.10.057.
[7] Deneke T, Khargi K, Lemke B, Lawo T, Lindstaedt M, Germing A, et al. Intra-operative cooled-tip radiofrequency linear atrial ablation to treat permanent atrial fibrillation. Eur Heart J 2007; 28:2909-14. doi:10.1093/eurheartj/ehm397.
[8] Ng F S, Camm A. Catheter ablation of atrial fibrillation. Clin Cardiol 2002; 25:384-94. doi:10.1002/clc.4950250808.
[9] Blaufox A D. Catheter Ablation of Tachyarrhythmias in Small Children. Indian Pacing Electrophysiol J 2005; 5:51-62.
[10] Vest J A, Seiler J, Stevenson W G. Clinical use of cooled radiofrequency ablation. J Cardiovasc Electrophysiol 2008; 19:769-73. doi:10.1111/j.1540-8167.2008.01193.x.
[11] H. Calkins. Catheter ablation to maintain sinus rhythm. Circulation 125, 1439-45 (2012).
[12] Erez A, Shitzer A. Controlled destruction and temperature distributions in biological tissues subjected to monoactive electrocoagulation. J Biomech Eng 1980; 102:42-9.
[13] Hornero, F. et al., Intraoperative Cryoablation of Atrial Fibrillation With the Old-Fashioned Cryode Tips: A Simple, Effective, and Inexpensive Method. Ann. Thorac. Surg. 84, 1408-1411 (2007).

What is claimed is:
1. A method of ablating myocardial tissue, comprising:
contacting a first electrode to a first section of myocardial tissue;
contacting a second electrode to a second section of myocardial tissue;

pairing pulse parameters of a nanosecond pulsed electric field with a configuration and/or spacing of the first and the second electrodes; and applying the nanosecond pulsed electric field between the first and the second electrodes to form a non-conducting lesion between epicardium and endocardium having substantially uniform ablated tissue volume with a lesion width between about 2 mm and about 6 mm.

2. The method of claim 1, wherein the pulse parameters of the nanosecond pulsed electric field comprise pulse amplitude or voltage.

3. The method of claim 1, the method comprises selecting electrode configuration and/or spacing between the first and the second electrode and selecting voltage based at least in part on the selected electrode configuration and/or spacing.

4. The method of claim 1, wherein pulse amplitude of the nanosecond pulsed electric field is in the range of about 1 kV to about 100 kV.

5. The method of claim 1, wherein the non-conducting lesion treats one or more of atrial fibrillation, ventricular tachycardia, or other arrhythmias.

6. The method of claim 1, the method comprising forming a plurality of adjacent, non-conducting lesions that are collectively sufficient to prevent or at least substantially reduce occurrence of arrhythmia conditions.

7. The method of claim 6, wherein at least some of the plurality of lesions are side-by-side or overlap.

8. The method of claim 1, wherein the contacting the first electrode to the first section of myocardial tissue comprises positioning the first electrode on a surface of the first section of the myocardial tissue.

9. The method of claim 1, wherein at least one of the first and the second electrodes penetrates the respective first or second sections of the myocardial tissue.

10. The method of claim 1, the method comprising using a catheter to deliver the first electrode and/or the second electrode to the myocardial tissue.

11. The method of claim 1, wherein at least the first section is a section comprising epicardium.

12. The method of claim 1, wherein the myocardial tissue comprises the epicardium, the endocardium, or both.

13. A method of ablating myocardial tissue, comprising:
contacting a first electrode to a first section of myocardial tissue;
contacting a second electrode to a second section of myocardial tissue;
applying a nanosecond pulsed electric field between the first and the second electrodes to form a non-conducting lesion in myocardial tissue having substantially uniform ablated tissue volume;
wherein a width of the non-conducting lesion is controlled at least in part by i) pulse parameters and ii) configuration and/or spacing between the first and second electrodes.

14. The method of claim 13, wherein the myocardial tissue comprises epicardium, endocardium, or both.

15. A system for ablating myocardial tissue, the system comprising:
a set of electrodes comprising a first electrode and a second electrode, the set of electrodes has a configuration such that at least one of the first electrode and the second electrode is positioned in contact with endocardium;
a pulse generator configured to generate a nanosecond pulsed electric field between the first and the second electrodes,
wherein the system is configured to apply the nanosecond pulsed electric field between the first electrode and the second electrode to form a non-conducting lesion in myocardial tissue having substantially uniform ablated tissue volume based at least in part on pairing configuration and/or spacing of the first and second electrodes with pulse parameters of the nanosecond pulsed electric field.

16. The system of claim 15, wherein the set of electrodes is on a supporting member such that the first electrode and the second electrode are substantially parallel.

17. The system of claim 15, wherein a diameter of either one or both of the first and the second electrodes is in the range from about 100 μm to about 1000 μm.

18. The system of claim 15, wherein at least one of the first and the second electrode is a penetrating electrode or wherein at least one of the first and the second electrode is a non-penetrating electrode.

19. The system of claim 15, wherein the system is configured to form the non-conducting lesion across a thickness of myocardial tissue having substantially uniform ablated tissue volume.

20. The system of claim 15, wherein the system is configured to form the non-conducting lesion having substantially uniform ablated tissue volume in about 1 to 2 seconds per site treated.

21. The system of claim 15, wherein at least one of the first electrode and the second electrode has an enlarged tissue contact area.

22. The system of claim 15, wherein the system is configured to pair the configuration of the set of electrodes and/or a spacing between the first and the second electrodes with a pulse amplitude or voltage of the electric field to create a desired substantially uniform ablated tissue volume.

23. The system of claim 22, wherein pulse amplitude is between 1 kV and 100 kV and the substantially uniform ablated tissue volume has a width up to about 6 mm.

24. The system of claim 15, wherein the set of electrodes is configured for positioning to treat atrial fibrillation, ventricular tachycardia, or other arrhythmias.

25. The system of claim 15, wherein at least the first electrode is on a catheter.

* * * * *